(12) United States Patent
Lee et al.

(10) Patent No.: US 10,702,642 B2
(45) Date of Patent: Jul. 7, 2020

(54) BLOOD PUMP

(71) Applicant: SNU R&DB FOUNDATION, Seoul (KR)

(72) Inventors: Jung Chan Lee, Seoul (KR); Hee Chan Kim, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 156 days.

(21) Appl. No.: 16/064,004

(22) PCT Filed: Mar. 20, 2017

(86) PCT No.: PCT/KR2017/002981
§ 371 (c)(1),
(2) Date: Jun. 20, 2018

(87) PCT Pub. No.: WO2017/164599
PCT Pub. Date: Sep. 28, 2017

(65) Prior Publication Data
US 2018/0369467 A1 Dec. 27, 2018

(30) Foreign Application Priority Data
Mar. 20, 2017 (KR) .................. 10-2016-0035234

(51) Int. Cl.
*A61M 1/12* (2006.01)
*A61M 1/10* (2006.01)
*F04D 13/02* (2006.01)

(52) U.S. Cl.
CPC ........ *A61M 1/1031* (2014.02); *A61M 1/1012* (2014.02); *F04D 13/024* (2013.01); *F04D 13/026* (2013.01)

(58) Field of Classification Search
CPC .. A61M 1/1031; A61M 1/1012; A61M 1/101; A61M 1/122; A61M 1/1036; A61M 1/1029; F04D 13/026; F04D 13/024
See application file for complete search history.

(56) References Cited

U.S. PATENT DOCUMENTS

2007/0276480 A1* 11/2007 Tansley ............... A61M 1/1017
623/3.13
2013/0331934 A1* 12/2013 Kabir ..................... A61F 2/24
623/3.11

FOREIGN PATENT DOCUMENTS

JP 2002-531184 A 9/2002
JP 2003-062064 A 3/2003
(Continued)

OTHER PUBLICATIONS

International Search Report in International Application No. PCT/KR2017/002981, dated Jul. 27, 2017.

*Primary Examiner* — Rex R Holmes
(74) *Attorney, Agent, or Firm* — Park, Kim & Suh, LLC

(57) ABSTRACT

The present invention relates to a blood pump. The blood pump according to the present invention includes: a housing including an inlet, through which blood flows, at an upper part of the housing and an outlet, through which the blood is discharged, along an edge of the housing; an impeller part, which is rotatable and disposed inside the housing, including a plurality of blades on the surface thereof so as to move the blood flowing in through the inlet toward the outlet by using a centrifugal force; a rotary shaft member disposed to penetrate the center part of the impeller part so as to support the impeller part to be rotatable which moves the blood to the lower part thereof; and a magnetic body disposed on the impeller part for rotating the impeller part in a predetermined direction according to a change in a magnetic field outside the housing.

10 Claims, 5 Drawing Sheets

(56) References Cited

FOREIGN PATENT DOCUMENTS

| | | | |
|---|---|---|---|
| JP | 4233475 | B2 | 3/2009 |
| JP | 5743567 | B2 | 7/2015 |
| KR | 10-1099832 | B1 | 12/2011 |

\* cited by examiner (a)          (b)

BLOOD PUMP

CROSS-REFERENCE TO RELATED APPLICATIONS

This application is the National Stage filing under 35 U.S.C. 371 of International Application No. PCT/KR2017/002981, filed on Mar. 20, 2017, which claims the benefit of Korean Patent Application No. 10-2016-0035234, filed on Mar. 24, 2016, the contents of which are all hereby incorporated by reference herein in their entirety.

TECHNICAL FIELD

The present invention relates to a blood pump, and more particularly, to a centrifugal blood pump which moves blood using a centrifugal force.

BACKGROUND ART

In general, a medical blood pump used in medical devices such as ventricular assist devices and extracorporeal circulation support devices may be divided into a pulsatile flow type and a continuous flow type. Here, a centrifugal blood pump which is the continuous flow type has a simpler structure than that of the pulsatile flow type and excellent mechanic performance and thus is widely used for the extracorporeal circulation support device which is used for a short period of time.

In the above described centrifugal blood pump, a one-sided impeller is mostly used to secure a space for forming magnetic coupling, and a space having a relatively thin gap exists at a side where the magnetic coupling is disposed. In the space, a flow does not occur so that when the impeller rotates at high speed, a pressure difference generates between the upper part of the pump and the space and thereby, performance of the pump may be significantly lowered.

In order to prevent this, when a penetration hole which penetrates a space between the upper part and the lower part is formed in the impeller, a flow occurs from the upper part to lower part and thus, above described problem may be solved. However, in such structure, when blood flows through the penetration hole, the blood may remain inside the penetration hole and thus, a thrombus may be formed. In order to prevent this, although the penetration hole is sealed, the sealed part may be damaged or cracked and a thrombus may be also formed.

Also, in terms of performance of the centrifugal blood pump, hemodynamic performance and blood compatibility are especially important. In order to generate sufficient blood flow rate, an impeller having a blade needs to be rotated at high speed. However, rotation of the impeller at high speed may cause damage to blood cells and thus blood compatibility may become worse. Accordingly, development on a blood pump which may prevent damage to blood cells and generate sufficient blood flow rate by rotating an impeller having a blade at low speed is needed.

DISCLOSURE

Technical Problem

The present invention provides a blood pump which may prevent a thrombus from being formed inside the blood pump.

The present invention also provides a blood pump which rotates an impeller at low speed to prevent damage to blood cells and generates sufficient blood flow rate.

Technical Solution

According to an aspect of the present invention, there is provided a blood pump including: a housing including an inlet, through which blood flows, at an upper part of the housing and an outlet, through which the blood is discharged, along an edge of the housing; an impeller part, which is rotatable and disposed inside the housing, including a plurality of blades on the surface thereof so as to move the blood flowing in through the inlet toward the outlet by using a centrifugal force; a rotary shaft member disposed to penetrate the center part of the impeller part so as to support the impeller part to be rotatable which moves the blood to the lower part thereof; and a magnetic body disposed on the impeller part for rotating the impeller part in a predetermined direction according to a change in a magnetic field outside the housing.

The rotary shaft member may include a rotary shaft supporting the impeller part to rotate, an exterior part covering at least a part of the rotary shaft and providing a flow path, through which the blood moves along the inside thereof; and a screw connecting the exterior part with the rotary shaft and moving the blood to the lower part along the flow path, when the rotary shaft rotates.

The impeller part may include upper and lower blades on both upper and lower surfaces thereof. Here, the upper blade formed on the upper surface of the impeller part and the lower blade formed on the lower surface of the impeller part may be disposed alternately.

The impeller part may include an upper impeller and a lower impeller, and the magnetic body disposed between the upper impeller and the lower impeller.

Advantageous Effects

According to the present invention, there is no space for blood to remain in the blood pump and thus, a thrombus is not formed. In particular, the blood does not remain inside the rotary shaft member by the screw disposed inside the rotary shaft member, which penetrates the impeller part, and thereby, forming of a thrombus may be suppressed.

Also, in the blood pump according to the present invention, the blades are disposed on both upper and lower surfaces of the impeller part so that performance of the pump improves and thereby, a high flow rate and high pressure head may be obtained at a relatively low rotation speed. Therefore, according to the present invention, blood cells may be prevented from being damaged and a sufficient blood flow rate may be obtained. In particular, high rotation speed is not needed to obtain a high flow rate and thus, hemolysis occurring due to a shearing force may be decreased.

Furthermore, according to the present invention, the blades on the upper and lower surfaces of the impeller part are disposed alternately so that a wavelength occurring due to the blades may be significantly decreased and thus, the blood may be smoothly provided.

BEST MODE

Hereinafter, a blood pump according to an embodiment of the present invention will be described in more detail with reference to the accompanying drawings.

Figure 1:
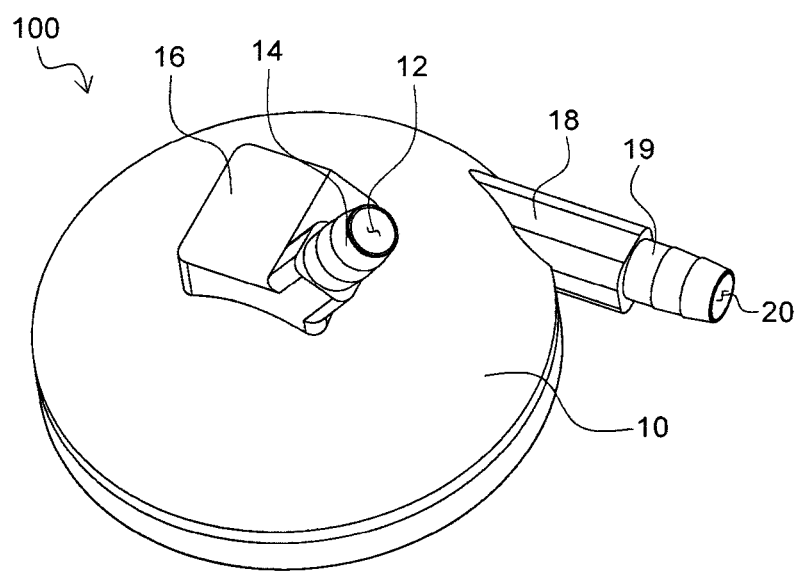
FIG. 1 is a perspective view of a blood pump according to an embodiment of the present invention.
Figure 2:
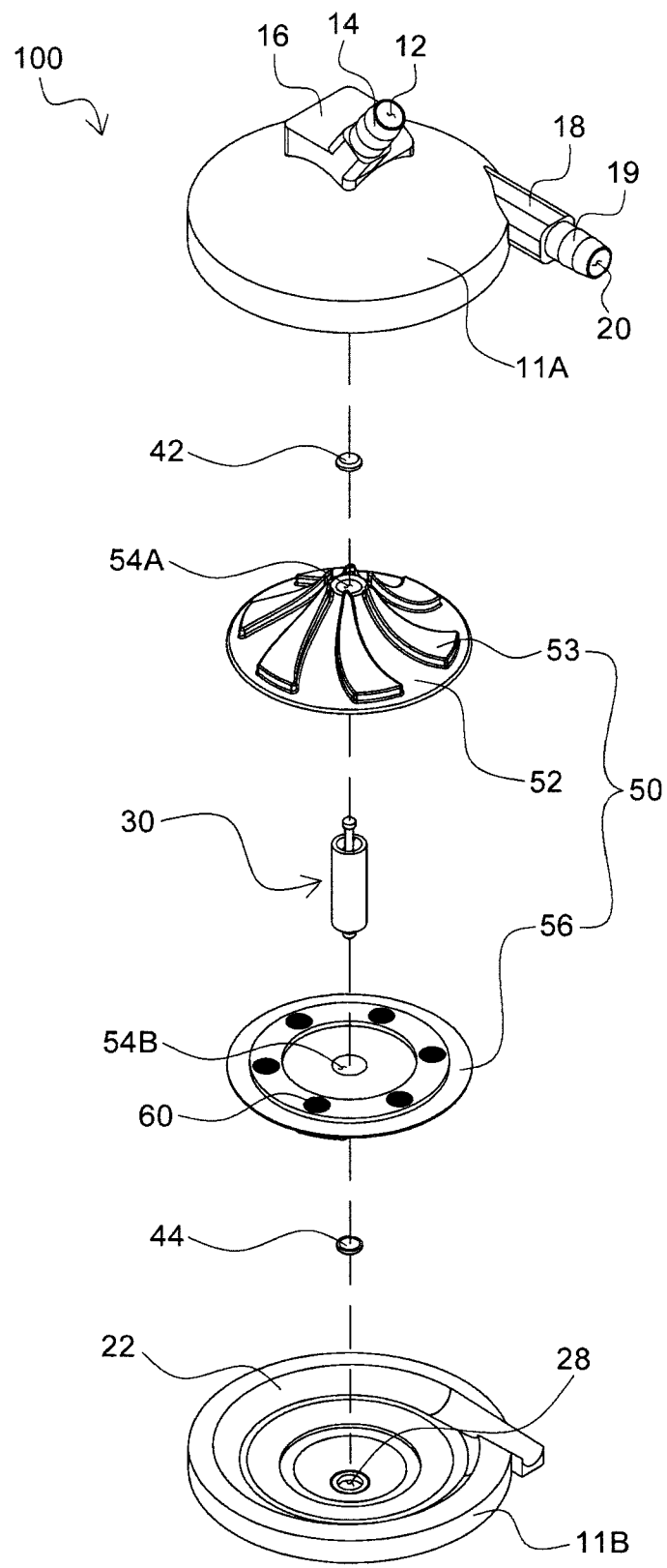
FIG. 2 is an exploded perspective view of the blood pump of FIG. 1.

FIG. 1 is a perspective view of a blood pump 100 according to an embodiment of the present invention and FIG. 2 is an exploded perspective view of the blood pump 100 of FIG. 1.

Referring to FIGS. 1 and 2, the blood pump 100 includes a housing 10, an impeller part 50, a rotary shaft member 30, and a magnetic body 60, wherein the housing 10 includes an inlet 12, through which blood flows, at an upper part of the housing 10 and an outlet 20, through which the blood is discharged, along an edge of the housing 10, the impeller part 50, which is rotatable and disposed inside the housing 10, includes a plurality of blades 53 and 58 on the surface thereof so as to move the blood flowing in through the inlet 12 toward the outlet 20 by using a centrifugal force, the rotary shaft member 30 disposed to penetrate the center part of the impeller part 50 so as to support the impeller part 50 to be rotatable moves the blood to the lower part thereof, and the magnetic body 60 disposed on the impeller part 50 rotates the impeller part 50 in a predetermined direction according to a change in a magnetic field outside the housing 10.

The housing 10 is the exterior of the blood pump 100 and includes an accommodation space 13 (refer to FIG. 6) to which the impeller part 50 and the rotary shaft member 30 may be installed, inside the housing 10. In this case, in order to facilitate manufacturing of the housing 10, the housing 10 includes an upper housing 11A and a lower housing 11B connected to the lower part of the upper housing 11A. A space between the upper housing 11A and the lower housing 11B is the accommodation space 13. The housing 10 may be formed using synthetic resins and a material to form the housing 10 is not restricted in the present invention.

The inlet 12, through which blood flows, is disposed at the upper part of the housing 10 and the outlet 20 is disposed along a side edge of the housing 10. When blood flows in through the inlet 12, the inlet 12 is disposed at the upper part of the housing 10 and thereby, the inlet 12 makes the blood moving toward the impeller part 50 disposed inside the housing 10. Also, when the impeller part 50 rotates, the outlet 20 is disposed along a side edge of the housing 10 and the blood is discharged through the outlet 20 outside the housing 10 by a centrifugal force.

More specifically, the housing 10 includes a projecting part 16 at the upper part thereof and a first connecting part 14 extended in a fixed length from the projecting part 16. In this case, an end part of the first connecting part 14 performs the role of the inlet 12. The first connecting part 14 may be connected to a tube so that blood may be provided. Also, the housing 10 includes an extended part 18 along the side thereof and a second connecting part 19 projected in a fixed length from the extended part 18. Here, an end part of the second connecting part 19 performs the role of the outlet 20 and the second connecting part 19 may be connected to a tube, through which the blood discharged through the outlet 20 may move.

The rotary shaft member 30 is disposed inside the housing 10 and is rotatable. When the impeller part 50 rotates, the rotary shaft member 30 becomes an axis. That is, when the rotary shaft member 30 rotates inside the housing 10, the impeller part 50 is connected to the outer circumference of the rotary shaft member 30 and rotates.

In order to rotate the rotary shaft member 30, an upper bearing 42 and a lower bearing 44 are respectively disposed at the upper part and the lower part of the rotary shaft member 30. Here, the upper bearing 42 and the lower bearing 44 may be each inserted into groove parts 28 respectively formed on the inner sides of the upper housing 11A and the lower housing 11B.

Figure 3:
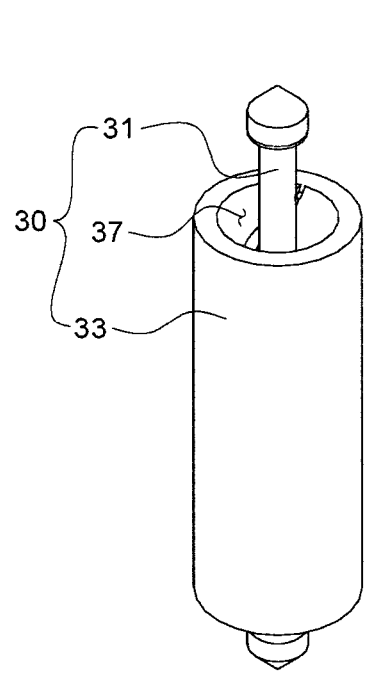
FIG. 3 is an enlarged view of a rotary shaft member of the blood pump of FIG. 1.
Figure 3:
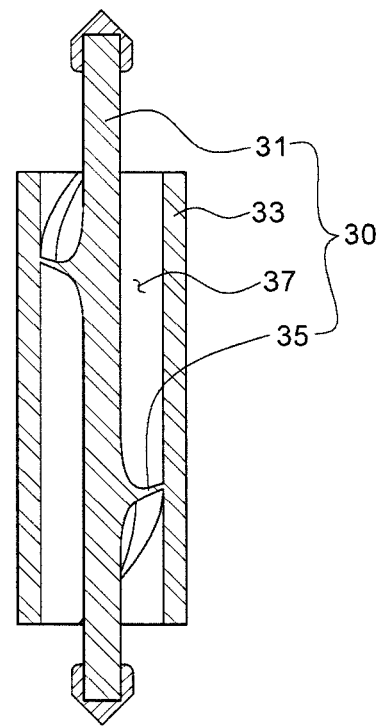

FIG. 3 is an enlarged view of the rotary shaft member 30. FIG. 3A is a perspective view of the rotary shaft member 30 and FIG. 3B is a cross-sectional perspective view of the rotary shaft member 30.

Referring to FIG. 3, the rotary shaft member 30 includes a rotary shaft 31, an exterior part 33, and a screw 35, wherein the rotary shaft 31 supports the impeller part 50 to rotate, the exterior part 33 covers at least a part of the rotary shaft 31 and provides a flow path 37, through which the blood moves along the inside thereof, and the screw 35 connects the exterior part 33 with the rotary shaft 31 and moves the blood to the lower part along the flow path 37, when the rotary shaft 31 rotates.

The rotary shaft 31 is extended in a fixed length and is connected to each of the upper bearing 42 and lower bearing 44 so as to be rotatable. The exterior part 33 is spaced apart from the rotary shaft 31 by a fixed interval and covers at least a part of the rotary shaft 31. Here, the flow path 37, through which the blood moves, is formed inside the exterior part 33.

The rotary shaft 31 and the exterior part 33 are connected with each other by the screw 35 and the number of the screw may be the plural. The screw 35 connects the rotary shaft 31 with the exterior part 33. Also, when the rotary shaft 31 rotates, the screw 35 moves the blood flowing in the flow path 37 through the upper part of the flow path 37 to the lower part along the flow path 37. Accordingly, when the blood pump 100 according to the present invention includes the rotary shaft member 30, which performs a role of the center axis of rotation through penetration holes 54A and 54B (refer to FIG. 2) each formed at the center of the impeller part 50, the blood does not remain in the flow path 37 disposed inside the rotary shaft member 30 and thus, a thrombus may be prevented.

The blood moved to the lower part through the flow path 37 of the rotary shaft member 30 moves toward the outlet 20 by rotation of the impeller part 50 and this will be described in more detail below.

Referring back to FIG. 2, the impeller part 50 includes the penetration holes 54A and 54B at the center thereof and the rotary shaft member 30 is inserted and fixed to the penetration holes 54A and 54B. Accordingly, when the rotary shaft member 30 rotates, the impeller part 50 also rotates.

The impeller part 50 includes the plurality of blades 53 and 58 on the surface thereof. When the blood is provided through the inlet 12, the impeller part 50 rotates in a predetermined direction and the blood moves toward the outlet 20 by a centrifugal force generated by the blades 53 and 58 of the impeller part 50.

Figure 4:
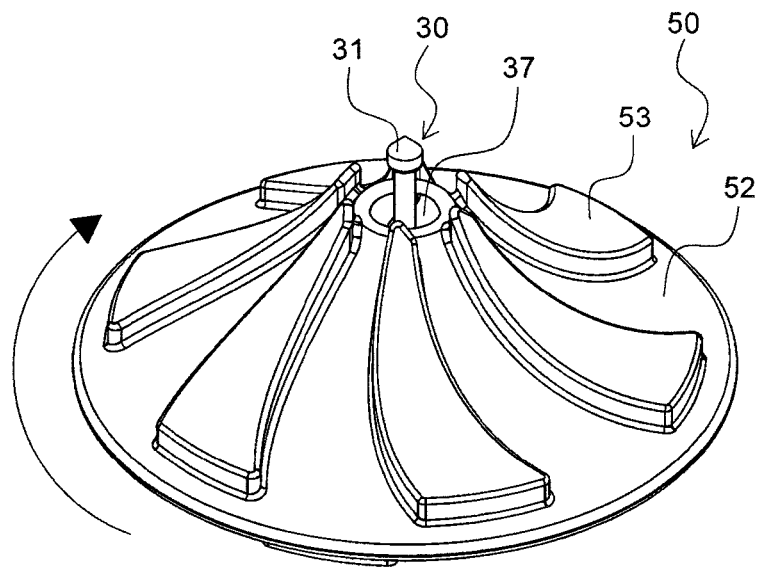
FIG. 4 is a perspective view of an impeller part of the blood pump of FIG. 1 viewing from the top.
Figure 5:
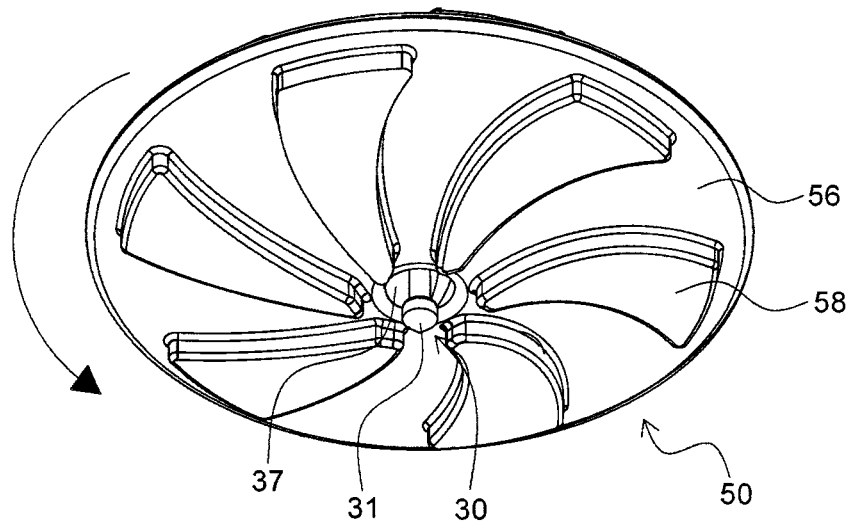
FIG. 5 is a perspective view of an impeller part of the blood pump of FIG. 1 viewing from the bottom.

FIG. 4 is a perspective view of the impeller part 50 viewing from the top and FIG. 5 is a perspective view of the impeller part 50 viewing from the bottom.

Referring to FIGS. 4 and 5, the blades 53 and 58 may be both formed on the upper surface and the lower surface of the impeller part 50. The upper blade 53 formed on the upper surface of the impeller part 50 moves the blood provided to the upper surface of the impeller part 50 through the inlet 12 toward the outlet 20.

The lower blade 58 formed on the lower surface of the impeller part 50 moves the blood moved to the lower part of the accommodation space 13 of the housing 10 by the rotary shaft member 30 toward the outlet 20. In this case, in order to smoothly move the blood by the lower blade 58 formed on the lower surface of the impeller part 50, a guide flow path 22 (Refer to FIG. 2) to guide the flow of the blood may be formed on the bottom of the accommodation space 13 of the housing 10. That is, when the impeller part 50 rotates, the blood placed at the bottom of the accommodation space 13 moves by the rotation of the lower blade 58 and at this time, the blood moves along the guide flow path 22 so as to move toward the outlet 20.

Accordingly, since the blades 53 and 58 are both formed on the upper surface and the lower surface of the impeller part 50 inside the blood pump 100 according to the present invention, the blood does not remain inside the housing 10 and furthermore, the blood may be efficiently provided.

In a centrifugal pump including conventional blades, when the blades rotate, waves may occur in an outlet by rotation of the blades and thus, blood may not be smoothly provided.

In the blood pump 100 according to the present invention, the upper blade 53 formed on the upper surface of the impeller part 50 and the lower blade 58 formed on the lower surface of the impeller part 50 may be disposed alternately. That is, when the blades 53 and 58 are disposed by placing the penetration holes 54A and 54B at the center, the upper blade 53 formed on the upper surface of the impeller part 50 and the lower blade 58 formed on the lower surface of the impeller part 50 may be disposed alternately. As described above, since the blades 53 and 58 respectively disposed on the upper and lower surfaces of the impeller part 50 are alternately disposed, a wavelength occurring due to the blades 53 and 58 may be significantly decreased.

Referring back to FIG. 2, the impeller part 50 may be formed as a single member, however, in order to facilitate manufacturing of the impeller part 50, the impeller part 50 may include an upper impeller 52 and a lower impeller 56. The lower impeller 56 is connected to the lower part of the upper impeller 52 to manufacture the impeller part 50.

The impeller part 50 may include a plurality of magnetic bodies 60 and the magnetic bodies 60 rotate the impeller part 50 in a predetermined direction according to a change in a magnetic field outside the housing 10. That is, when a change in a magnetic field is generated outside the housing 10, a force acts to the magnetic bodies 60 in a particular direction and thereby, the impeller part 50 rotates.

The magnetic bodies 60 may be embedded inside the impeller part 50. When the impeller part 50 includes the upper impeller 52 and the lower impeller 56, the magnetic bodies 60 may be disposed between the upper impeller 52 and the lower impeller 56. Accordingly, when the upper impeller 52 and the lower impeller 56 are assembled, the magnetic bodies 60 are disposed between the upper impeller 52 and the lower impeller 56 and thus, the magnetic bodies 60 may be easily installed to the inside of the impeller part 50.

Figure 6:
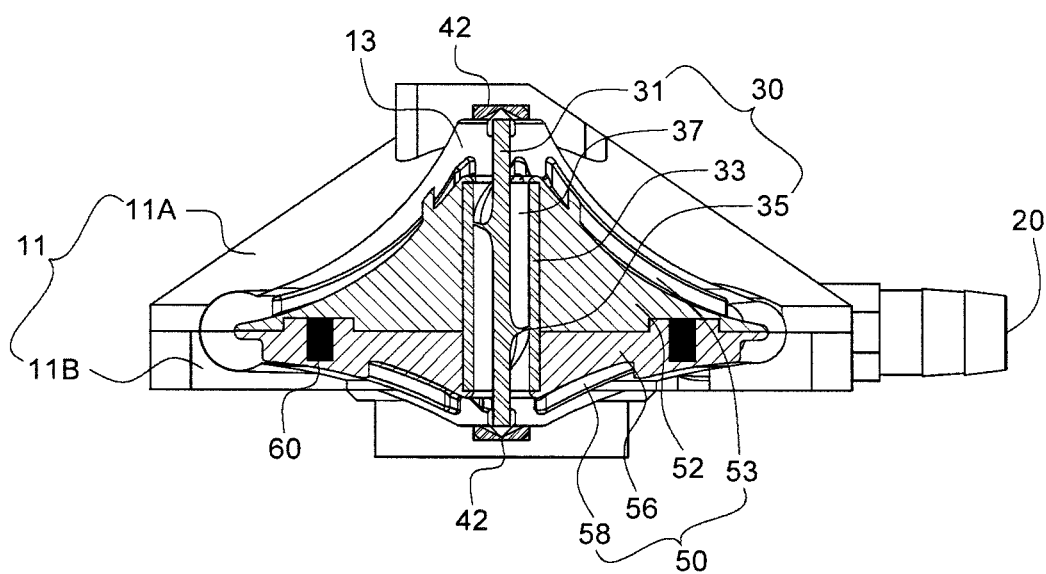
FIG. 6 is a side cross-sectional view of the blood pump of FIG. 1.

Hereinafter, the operation of the blood pump 100 according to the present invention will be described with reference to FIG. 6. FIG. 6 is a side cross-sectional view of the blood pump 100.

Referring to FIG. 6, a relatively large amount of blood from among the blood provided to the accommodation space 13 inside the housing 10 through the inlet 12 is provided to the upper surface of the impeller part 50. Here, the impeller part 50 rotates in a direction predetermined by the magnetic bodies 60 and the blood moves toward the outlet 20 by the upper blade 53 formed on the upper surface of the impeller part 50.

A part of the blood from among the blood provided to the inside of the housing 10 is provided to the inside of the rotary shaft member 30, which performs a role of the center axis of rotation of the impeller part 50. Here, the blood provided to the inside of the rotary shaft member 30 rapidly moves to the lower part by the screw 35 of the rotary shaft member 30. The blood moved to the accommodation space 13 inside the housing 10 moves toward the outlet 20 by the lower blade 58 formed on the lower surface of the impeller part 50.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A blood pump comprising:
   a housing including an inlet, through which blood flows, at an upper part of the housing and an outlet, through which the blood is discharged, at an edge of the housing;
   an impeller rotatably disposed inside the housing, the impeller including a plurality of blades on a surface thereof so as to move the blood flowing in through the inlet toward the outlet by using a centrifugal force;
   a rotary shaft member disposed to penetrate a center part of the impeller so as to support the impeller to be rotatable, the rotary shaft member configured to move the blood toward to a lower part of the housing; and
   a magnetic body provided to the impeller for rotating the impeller in a predetermined direction according to a change in a magnetic field outside the housing
   wherein the rotary shaft member includes:
      a rotary shaft supporting the impeller to rotate;
      a tube enclosing at least a part of the rotary shaft and providing a flow path, through which the blood moves along an inside thereof, the tube being inserted into a through hole which is formed at the center part of the impeller; and
      a screw connecting the tube and the rotary shaft, the screw being configured to move the blood to the lower part of the housing along the flow path while rotating along with the rotary shaft, and
   wherein the rotary shaft includes a first end and a second end located opposite to the first end, and the first and second ends of the rotary shaft are rotatably supported by the upper and lower parts of the housing, respectively.

2. The blood pump of claim 1, wherein the impeller comprises upper and lower blades on both upper and lower surfaces thereof.

3. The blood pump of claim 2, wherein the upper blade formed on the upper surface of the impeller and the lower blade formed on the lower surface of the impeller are disposed alternately.

4. The blood pump of claim 2, wherein the impeller includes an upper impeller and a lower impeller, and the magnetic body is disposed between the upper impeller and the lower impeller.

5. The blood pump of claim 1, wherein the housing includes first and second recesses formed at the upper and lower parts thereof, respectively, and the first and second ends of the rotary shaft are inserted into the first and second recesses, respectively.

6. The blood pump of claim 5, wherein the housing includes first and second bearings accommodated within the first and second recesses, respectively to rotatably support the first and second ends of the rotary shaft, respectively.

7. The blood pump of claim 1, wherein the screw is configured to feed the blood to a space between a lower part of the impeller and the lower part of the housing.

8. The blood pump of claim 1, wherein the housing includes a guide path formed at the lower part thereof, the guide path being configured to guide the blood between a lower part of the impeller and the lower part of the housing to flow toward the outlet.

9. The blood pump of claim 8, wherein the guide path comprises a recess formed on a surface of the lower part of the housing which faces the lower part of the impeller, the recess extending along a circumference of the lower part of the housing and connected to the outlet.

10. The blood pump of claim 1, wherein the magnetic body is disposed within the impeller so as not to be exposed outside the impeller.

* * * * *